US00PP36216P2

(12) United States Plant Patent
Boxriker

(10) Patent No.: US PP36,216 P2
(45) Date of Patent: Oct. 22, 2024

(54) ***DIANTHUS* PLANT NAMED 'KLEDP23480'**

(50) Latin Name: ***Dianthus caryophyllus* L.**
Varietal Denomination: KLEDP23480

(71) Applicant: KLEMM + SOHN GMBH & CO. KG, Stuttgart (DE)

(72) Inventor: Maike Boxriker, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/417,716

(22) Filed: Jan. 19, 2024

(51) Int. Cl.
*A01H 5/02* (2018.01)
*A01H 6/30* (2018.01)

(52) U.S. Cl.
USPC ..... Plt./273

(58) Field of Classification Search
USPC ..... Plt./272, 273
See application file for complete search history.

*Primary Examiner* — Susan McCormick Ewoldt
(74) *Attorney, Agent, or Firm* — Weatherly IP Solutions, LLC; James M. Weatherly

(57) ABSTRACT

A new *Dianthus* plant designated 'KLEDP23480' particularly distinguished by hot pink flowers with a light border and medium earliness, is disclosed.

1 Drawing Sheet

Genus and species: *Dianthus caryophyllus* L.
Variety denomination: 'KLEDP23480'.

BACKGROUND OF THE NEW PLANT

The present invention comprises a new and distinct variety of *Dianthus*, botanically known as *Dianthus caryophyllus* L. and hereinafter referred to by the variety name 'KLEDP23480'. 'KLEDP23480' originated from a cross conducted in May of 2019 in Stuttgart, Germany between the proprietary *Dianthus* female parent 'DCP-2017-7258' (unpatented) and the proprietary *Dianthus* male parent 'DCP-2017-7240' (unpatented). The seeds from this cross were sown in Stuttgart, Germany and a single plant was selected in May 2019.

In July 2019, 'KLEDP23480' was first vegetatively propagated by vegetative stem cuttings in Stuttgart, Germany. 'KLEDP23480' was found to reproduce true to type in successive generations of asexual propagation in Stuttgart, Germany via vegetative cuttings.

SUMMARY

The following are the most outstanding and distinguishing characteristics of 'KLEDP23480' when grown under normal horticultural practices in Stuttgart, Germany.

1. Hot pink flowers with a light border; and
2. Medium earliness.

DESCRIPTION OF THE PHOTOGRAPH

This new *Dianthus* plant is illustrated by the accompanying photograph of a 12-week-old plant taken in April 2022 and grown in a greenhouse in Stuttgart, Germany. The colors shown are as true as can be reasonably obtained by conventional photographic procedures. The photograph is a whole plant photo of 'KLEDP23480' and shows the foliage, buds, and flowers.

DESCRIPTION

The following detailed descriptions set forth the distinctive characteristics of 'KLEDP23480'. The data which define these characteristics were collected from asexual reproductions carried out in Stuttgart, Germany. Data was collected in January 2024 from plants that were 23 weeks old and grown in a greenhouse. Color references are to The R.H.S. Colour Chart of The Royal Horticultural Society of London (R.H.S.), 5$^{th}$ edition (2007).

Classification:
- *Family.*—Caryophyllaceae.
- *Botanical.*—*Dianthus caryophyllus* L.
- *Designation.*—'KLEDP23480'.
- *Type.*—Pot carnation.

Parentage:
- *Female parent.*—*Dianthus* 'DCP-2017-7258' (unpatented).
- *Male parent.*—*Dianthus* 'DCP-2017-7240' (Unpatented).

Plant:
- *Propagation type.*—Vegetative cuttings.
- *Time to produce a rooted young plant.*—28 days.
- *Root description.*—Fine roots, RHS 155C.
- *Rooting habit shape.*—Lanceolate.
- *Plant form.*—Upright.
- *Plant height.*—13.0 cm.
- *Plant diameter or spread.*—24.0 cm.

Lateral branches/stems:
- *Shape of the branch in cross-section.*—Slightly angular.
- *Hollowness of the branch.*—Absent.
- *Length.*—11.0 cm.
- *Diameter.*—0.2 cm.
- *Internode length.*—3.5 cm.
- *Internode quantity per branch.*—4.
- *Number of internodes per branch/stem.*—4.
- *Node length.*—0.3 cm.
- *Node diameter.*—0.5 cm.
- *Texture.*—Smooth.
- *Color.*—RHS 137A.
- *Flower clustering on the lateral branch.*—In some lateral branches.

Foliage:
*Arrangement*.—Opposite.
*Length*.—5.6 cm.
*Width*.—0.6 cm.
*Shape*.—Obovate.
*Apex*.—Acute.
*Base*.—Obtuse.
*Margin*.—Entire.
*Texture* (*both upper and lower surfaces*).—Smooth.
*Cross-section of the leaf*.—Weakly concave.
*Curvature of the leaf*.—Absent.
*Glaucosity of the leaf*.—Weak.
*Leaf color* (*both immature and mature*).—Immature: Upper surface: RHS N137B. Lower surface: RHS 137A. Mature: Upper surface: RHS N137B. Lower surface: RHS 137A.
*Venation pattern*.—Absent.

Flowers:
*Flower type and habit*.—Semidouble sprays.
*Fragrance*.—Present.
*Position of the flowers compared to the foliage of the plant*.—Moderately above.
*Profile of both the upper and lower part in the lateral view*.—Concave.
*Diameter of the flower*.—5.1 cm.
*Natural flowering season*.—Spring to autumn.
*Number of flowers per spray*.—1.
*Flower longevity on the plant*.—14 days.

Buds:
*Length*.—1.4 cm.
*Diameter*.—0.8 cm.
*Shape*.—Elliptic.
*Color*.—RHS 138A.
*Extrusion of the styles at the bud stage*.—Absent.

Corolla:
*Quantity of petals and arrangement*.—18 and arranged in several whorls.
*Corolla height*.—2.5 cm.
*Petal length*.—4.3 cm.
*Petal width*.—2.5 cm.
*Petal shape*.—Obtuse.
*Petal apex*.—Obtuse.
*Petal base*.—Acute.
*Petal margin*.—Crenate.
*Depth of petal margin*.—Medium.
*Petal texture* (*both upper and lower surfaces*).—Smooth.
*Petal color*.—Immature: Upper surface: RHS 71A. Lower surface: RHS N155B. Mature: Upper surface: RHS N74A. Lower surface: RHS N155B.
*Macule*.—Present and border RHS N155B.
*Quantity of sepals and arrangement*.—Composed of 5 sepals. Longitudinal axis of the lobes of the calyx: Straight. Shape: Campanulate. Calyx height: 0.5 cm. Calyx diameter (at the apex): 0.5 cm. Sepal texture (both upper and lower surfaces): Smooth. Sepal color: Upper surface: RHS 138A. Lower surface: RHS 145A.
*Position of the outer lobes of the epicalyx in relation to the calyx*.—Adpressed and free.
*Apex shape of the outer lobes of the epicalyx*.—Medium acuminate.
*Tip length of the outer lobes of the epicalyx*.—0.4 cm.
*Apex shape of the inner lobes of the epicalyx*.—Short acuminate.
*Tip length of the inner lobes of the epicalyx*.—0.5 cm.

Peduncles:
*Length*.—0.2 cm.
*Diameter*.—0.2 cm.
*Strength*.—Strong.
*Texture*.—Smooth.
*Color*.—RHS 137C.

Reproductive organs:
*Stamens*.—Quantity per flower: 6. Filament length: 2.4 cm. Filament color: RHS 157A. Anther length: 0.2 cm. Anther diameter: 0.1 cm. Anther color: RHS 166D. Pollen amount: None observed.
*Pistils*.—Quantity per flower: 2. Length: 2.8 cm. Diameter: 0.1 cm. Stigma: Color: RHS NN155B. Shape: Filamentous. Length: 0.1 cm. Diameter: 0.1 cm. Style: Color: RHS NN155B. Length: 2.7 cm. Diameter: 0.1 cm. Ovary: Color: RHS144D. Width: 0.7 cm.

Seeds: None observed to date.

Disease and insect resistance: No particular disease or insect resistance observed.

COMPARISON OF 'KLEDP23480' WITH PARENTAL LINES AND KNOWN VARIETY

'KLEDP23480' is distinguished from the parents as described in Table 1.

TABLE 1

Comparison with Parental Lines

| Characteristic | 'KLEDP23480' | Female parent 'DCP-2017-7258' | Male parent 'DCP-2017-7240' |
|---|---|---|---|
| Flower | Light border | Light border | No border |
| Earliness | Medium early | Medium early | Late |
| Flower color | Hot pink | Pink | Hot pink |

'KLEDP23480' can be compared to the commercial *Dianthus* variety 'KLEDP07089' (unpatented). Differences between the varieties are described in Table 2.

TABLE 2

Comparison with Similar Variety

| Characteristic | 'KLEDP23480' | 'KLEDP07089' |
|---|---|---|
| Flower color | Hot Pink | Red |

I claim:

1. A new and distinct variety of *Dianthus* plant designated 'KLEDP23480' as illustrated and described herein.

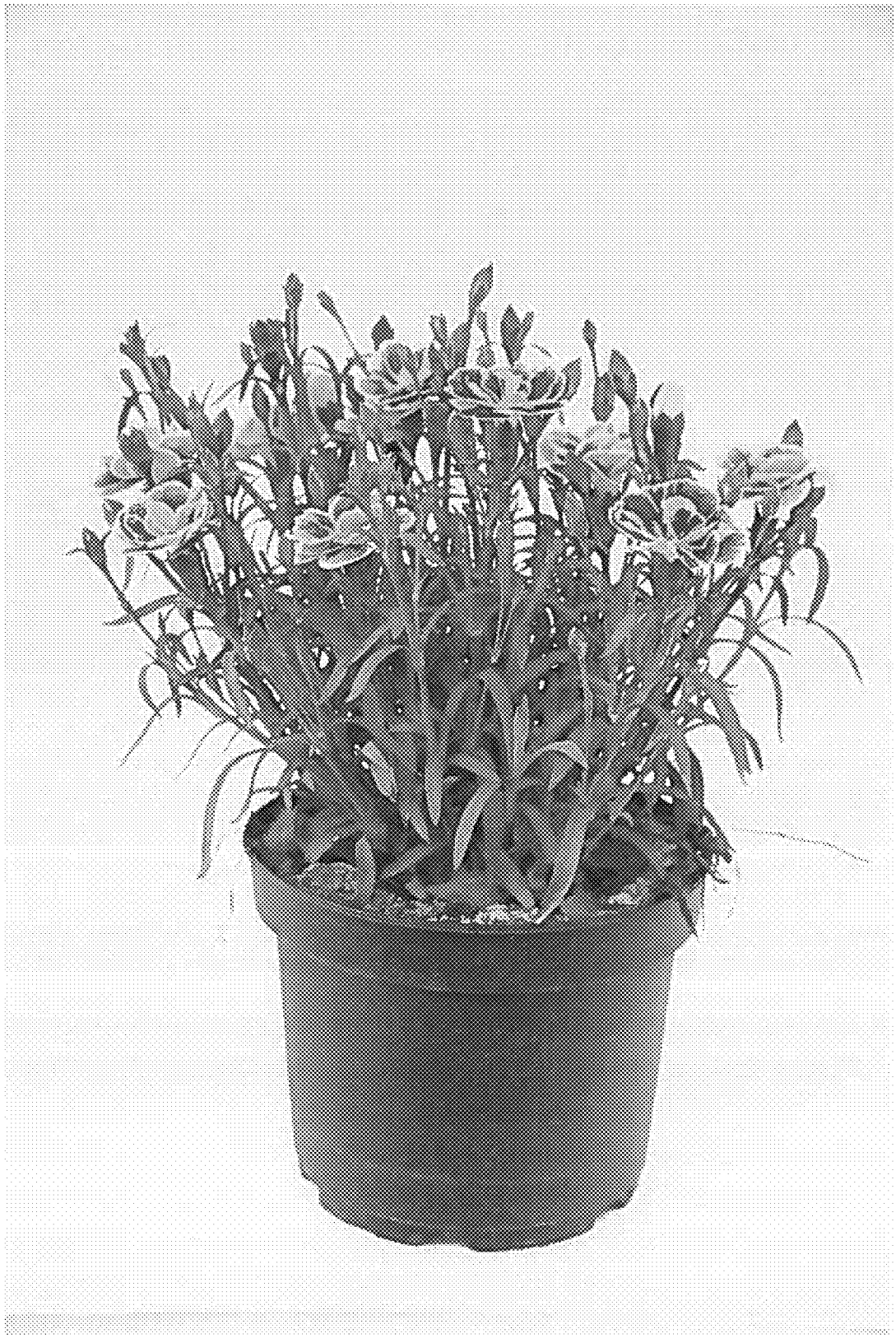

* * * * *